United States Patent [19]
Miyazaki et al.

[11] Patent Number: 5,332,803
[45] Date of Patent: Jul. 26, 1994

[54] PROCESSES FOR THE PREPARATION OF AMYLASE INHIBITOR

[75] Inventors: Toshiyuki Miyazaki, Fujimi; Ryuji Murayama, Hyogo; Toshihisa Morimoto, Tokyo, all of Japan

[73] Assignees: Nisshin Flour Milling Co., Ltd., Tokyo; Nagata Sangyo Co. Ltd., Shiso, both of Japan

[21] Appl. No.: 49,180

[22] Filed: Apr. 19, 1993

[30] Foreign Application Priority Data

Apr. 22, 1992 [JP] Japan ................. 4-127970

[51] Int. Cl.⁵ .......................... C07K 3/02; C07K 3/24; C07K 3/28; C07K 15/10
[52] U.S. Cl. .................................. 530/375; 530/374; 530/416; 530/419; 530/420
[58] Field of Search ............... 530/374, 375, 416, 419, 530/421; 514/2, 8, 12

[56] References Cited

U.S. PATENT DOCUMENTS

| | | | |
|---|---|---|---|
| 3,950,319 | 4/1976 | Schmidt et al. | 530/374 |
| 4,463,091 | 7/1984 | Harada et al. | 435/71.2 |
| 4,806,626 | 5/1989 | Maeda et al. | 530/375 |
| 5,084,275 | 1/1992 | Maeda et al. | 424/195.1 |

OTHER PUBLICATIONS

O'Donnell et al. "Purification & Properties of Anα-Amylase Inhibitor from Wheat" Biochim et Biophych Acta 422: 159-169 1976.
Petucci et al. "Further Characterization Studies of the α-Amylase Protein Inhibitor of Gel Electrophoretic Mobility 0.19 From The Wheat Kernal Bioch" et Biophysica 420 1976 288-297.
O'Connor et al. "Isolation & characterization of 4 Inhibitors From Wheat Flour which Display Differential Inhibition Specifities Human Salivay & Human Panereaticα-Amylase B et BA".
Harris et al. "Protein Purification Methods" pp. 204-207, 212-213 1989.
Annals N.Y. Academy of Science, vol. 121, p. 404 (1985).
Kakade et al., Cereal Chem., vol. 51, p. 376 (1974).

*Primary Examiner*—Jeffrey E. Russel
*Assistant Examiner*—Nancy J. Gromet
*Attorney, Agent, or Firm*—Abelman Frayne & Schwab

[57] ABSTRACT

A process for the preparation of an amylase inhibitor is disclosed which comprises the steps of:

(a) extracting wheat, wheat flour or wheat gluten with water, a dilute acid, a dilute alkali or an aqueous alcohol to produce a solution containing the amylase inhibitor;

(b) adding a polysaccharide to said solution to form an insoluble complex of the amylase inhibitor with the polysaccharide and separating the insoluble complex from the solution;

(c) dissolving or dispersing said complex in a solution, then separating the polysaccharide from the solution to collect a solution containing the amylase inhibitor; and (d) treating the collected solution with a cation exchanger to recover the amylase inhibitor from fractions that have not been adsorbed on the cation exchanger.

The amylase inhibitors produced by the above process possess a high amylase inhibitory activity but substantially no trypsin inhibitory activity, and are useful in the prophylaxis and treatment of diseases such as hyperglycemia, diabetes, hyperlipemia, arteriosclerosis and obesity.

6 Claims, No Drawings

PROCESSES FOR THE PREPARATION OF AMYLASE INHIBITOR

FIELD OF THE INVENTION

This invention relates to a process for the preparation of an amylase inhibitor from wheat, wheat flour or wheat gluten, to an amylase inhibitor produced by said process, to foods containing said amylase inhibitor added, and to agents for inhibiting an increase in blood glucose level and for controlling an insulin secretion, which comprise said amylase inhibitor as an active ingredient.

BACKGROUND OF THE INVENTION

In recent years, metabolic diseases including diabetes are on rapid increase as life has become richer in eating habits. Intake of excessive nutrients induces secretion of a larger amount of insulin to cause indirectly a collapse of metabolic balance, thus leading to a reduction of glucose tolerating function (hyperglycemia), diabetes, hyperlipemia, arteriosclerosis, etc. Especially in diabetic patents, the insulin function is insufficient and the glucose tolerance is lowered, so that blood glucose level is remarkably increased after meals to cause complications such as damages in blood capillary and arteriosclerosis.

For the prophylaxis and treatment of such diseases are effective foods or materials which can hardly induce an increase in blood glucose level or are capable of inhibiting a secretion of a large amount of insulin after uptake of necessary nutrition. Therefore, there is continuing need for a material capable of inhibiting the hydrolysis of the ingested starch into glucose and a material capable of saving an insulin secretion.

From the above aspects, various studies have been made on an amylase inhibitor being capable of inhibiting an activity of an amylase which hydrolyzes starch into glucose. Amylase inhibitors were reported to be contained in wheat. Since then, the amylase inhibitors of wheat origin have been investigated.

U.S. Pat. No. 3,950,319 discloses that the amylase inhibitor extracted from wheat with water, an acid or an aqueous alcohol is used for the treatment of diabetes, obesity and the like.

The prior amylase inhibitor of wheat origin does not achieve the effect as expected when orally administered. Further, it has the disadvantage of high cost and reduced inhibition of digestion to glucose, particularly for the digestion of heat cooked starch such as cooked rice.

SUMMARY OF THE INVENTION

We have found that an amylase inhibitor can be recovered selectively in a higher yield from wheat, wheat four or wheat gluten by adding to an aqueous extract thereof a polysaccharide such as sodium alginate to form an insoluble complex and separating the polysaccharide from the complex. Our further study of the amylase inhibitor as prepared above has revealed that it has a high amylase inhibitory activity, but has a considerable trypsin inhibitor activity.

As described above, the amylase inhibitor has an activity to inhibit the hydrolysis of starch into glucose, thereby enabling an inhibition of increase in blood glucose level, eventually saving of an insulin secretion. On the other hand, a trypsin inhibitor has generally an activity to promote a hypersecretion of pancreatic juice containing a large amount of amylase, and hence will obstruct saving of an insulin secretion achieved by an amylase inhibitor. Moreover, a trypsin inhibitor will interfere with an amylase inhibitory action of an amylase inhibitor and will induce hypertrophy of the pancreas, thus providing a risk factor for pancreatic cancer. Thus, it is not desired to intake such trypsin inhibitor over a long period of time.

Therefore, it is an object of this invention to provide a process for the preparation of an amylase inhibitor having a very high amylase inhibitory activity but no or very little trypsin inhibitory activity from an extract of wheat, wheat flour or wheat gluten. Another object of the invention is to provide an amylase inhibitor which has a high inhibitory activity against amylases contained in pancreatic juice and is highly effective for saving an insulin secretion.

Thus, the invention relates to a process for the preparation of an amylase inhibitor which comprises the steps of:

(a) extracting wheat, wheat flour or wheat gluten with water, a dilute acid, a dilute alkali or an aqueous alcohol to produce a solution containing the amylase inhibitor;

(b) adding a polysaccharide to said solution to form an insoluble complex of the amylase inhibitor with the polysaccharide and separating the insoluble complex from the solution;

(c) dissolving or dispersing said complex in a solution, then separating the polysaccharide from the solution to collect a solution containing the amylase inhibitor; and (d) treating the collected solution with a cation exchanger to recover the amylase inhibitor from fractions that have not been adsorbed on the cation exchanger.

The invention also relates to an amylase inhibitor prepared by the above process, a food containing the same as well as an agent for inhibiting an increase in blood glucose level and for controlling an insulin secretion which comprises the amylase inhibitor as an active ingredient.

DETAILED DESCRIPTION OF THE INVENTION

Water is most preferable for the extraction of an amylase inhibitor used in step (a), but a dilute acid, a dilute alkali or an aqueous alcohol may be used in place of water. For the dilute acid is conveniently employed an acidic aqueous solution at a pH of about 2-6 adjusted with an inorganic acid such as hydrochloric or phosphoric acid or an organic acid such as acetic acid. For the dilute alkali is conveniently used an alkaline aqueous solution at a pH of 8-10 adjusted with a base such as ammonia or sodium hydroxide. For the aqueous alcohol is conveniently used an aqueous alcohol solution with an alcohol concentration of about 1-50%. The alcohols used include methanol, ethanol, isopropyl alcohol and the like.

In the extraction treatment, several methods can be employed such as (i) a method which comprises extracting wheat, wheat flour or wheat gluten with a sufficient amount (usually about 3-50 times amount) of water, a dilute acid, a dilute alkali or an aqueous alcohol, while stirring usually at a temperature of about 10°-40° C. followed by removal of solids by an appropriate means such as centrifugal separation, filtration or standing to obtain a solution containing an amylase inhibitor and (ii) a method using as an amylase inhibitor-containing solution, the waste liquid or water washings of the dough or batter discharged in the process of producing starch or gluten from wheat flour.

The method (ii) is advantageous for efficient use of the waste liquid (water washings) discharged in the production of starch and gluten by Martin's and Batter's methods. The method (ii) comprises kneading a mixture of wheat flour and water to form a dough or batter, aging it to thoroughly hydrate gluten, repeatedly washing the dough with added water, separating the gluten and starch milk (gluten wash liquid) and recovering starch from the starch milk by such means as mechanical separation. The waste liquid produced from washing with water contains an amylase inhibitor and can serve as an amylase inhibitor-containing solution used in step (a) of the present invention.

The amylase inhibitor-containing solution extracted in step (a) (called hereafter "extract solution" for convenience) may directly be fed to the subsequent step [step (b)] in which an insoluble complex with a polysaccharide is formed. However, the extract solution often contains contaminants such as soluble proteins, soluble saccharides, inorganic salts and soluble dyes. Therefore, it is desirable to remove those contaminants, particularly soluble proteins before passing to step (b). The method for removing contaminants can include heating the extract solution at 70°-90° C., preferably 85°-90° C., or adjusting the pH of the extract solution to the range between 2 and 4 or a combination of the heating and pH adjustment. In this process, the contaminants such as soluble proteins are denatured and insolubilized, which can be separated out from the extract solution by an appropriate means.

If necessary, the extract solution from which contaminants have been removed may be passed through a microfiltration membrane such as a porous macromolecular membrane having a pore size of 0.2 $\mu$m or a ceramic filter for the exclusion of microbials.

Subsequently, the extract solution is passed to step (b) in which said solution is mixed with a polysaccharide capable of forming an insoluble complex with the solution. The kind of polysaccharides used in step (b) can be varied depending on the temperature and pH of the extract solution. Concrete examples of polysaccharides include those with a cation exchange function such as sodium alginate, carboxymethylcellulose, $\kappa$-carrageenan, $\nu$-carrageenan and $\lambda$-carrageenan; pectin; xanthan gum; and gellan gum, sodium alginate being preferable from the aspect of providing an increased yield of the insoluble complex.

Preferably, polysaccharides are added in an amount of 50–600 ppm to the extract solution. Formation of the insoluble complex is preferably performed while maintaining the pH of the extract solution within a range of about 1–6, and preferably at room temperature or under cooling, although it may also be conducted under heating. Generally, the insoluble complex is formed by adding the polysaccharide to the extract solution, then adjusting the pH of the extract solution to 2–5 and stirring the mixture at room temperature or under cooling (usually at about 1°–30° C.) for a time from several ten minutes to several hours. The resultant insoluble complex is separated from the extract solution by filtration, centrifugal separation or other suitable methods.

Subsequently, the insoluble complex separated in step (b) is dissolved or dispersed in a solution, e.g. water; an aqueous solution of a weak alkali such as ammonia or ammonium hydrogencarbonate; an aqueous solution of salts containing neither calcium nor potassium; and the like. This operation is conducted at room temperature or preferably at elevated temperatures, usually at a temperature of 30° to 70° C.

Then, a metal ion such as potassium, calcium and magnesium ions is added to the solution or dispersion containing the amylase inhibitor and polysaccharide to cause the gelation of the polysaccharide, thus forming solid insolubles, while leaving the amylase inhibitor dissolved in the solution. A solution containing the amylase inhibitor can be recovered by separating and removing the polysaccharide gel from the solution by any suitable method (step (c)).

Of the polysaccharides mentioned above, especially sodium alginate, $\kappa$-carrageenan, $\nu$-carrageenan and $\lambda$-carrageenan can form an insoluble gel easily by addition of metal ions such as potassium, calcium or magnesium ions.

Subsequently, the solution containing an amylase inhibitor from which polysaccharide has been removed is treated with a cation exchanger to recover the desired amylase inhibitor from fractions not adsorbed on the cation exchanger [step (d)].

In that case, the amylase inhibitor-containing solution obtained in step (c) may be treated as such with a cation exchanger in step (d), or be subjected to other purification step, if necessary, before the cation exchanger treatment. In general, the treatment with a cation exchanger after other purification step is desirable for the production of an amylase inhibitor having a higher amylase inhibitory activity and containing a lower content of undesired substances such as a trypsin inhibitor.

When other purification steps are applied prior to the cation exchanger treatment of step (d), the solution containing the amylase inhibitor obtained in step (c) is heated, for example, at 70°–90° C. to denature and solidify contaminants still remaining in the solution, such as heat unstable proteins and the solids are separated and removed. The remaining solution is desirably subjected to further treatments such as passing through an ultrafiltration membrane or gel filtration chromatography to remove excess salts and other low molecular contaminants before concentration. As the ultrafiltration membranes are preferably used those comprising a polyacrylonitrile, polyolefin, polysulfine, polyimide or cellulose material and having a fractionation molecular weight of 20000 Dalton cut off.

In treating the solution containing the amylase inhibitor with a cation exchanger, cation exchangers such as polymer cation exchange resins, silicic acid and aluminum silicate may be employed. Polymer cation exchange resins such as Diaion HPK-55 (trade name; manufactured by Mitsubishi Kasei Kogyo K.K.) are preferable. The treatment with a cation exchanger may be carried out either by a batch process which includes stirring a cation exchanger added to the solution or by a continuous process which includes passing the solution through a cation exchanger packed in a column, the continuous process being preferred. In the treatment with a cation exchanger, the solution containing the amylase inhibitor is preferably adjusted to pH of 6–9, by which the amylase inhibitor in the solution is recovered as fractions passing through the column or as fractions not adsorbed on the cation exchanger (in the case of a batch process). Through this cation exchanger treatment, a harmful trypsin inhibitor is adsorbed on the cation exchanger and an amylase inhibitor containing no or very little trypsin inhibitor can be recovered in a high yield.

The fractions not adsorbed on the cation exchanger which are obtained in the above cation exchanger treatment [step (d)] can be subjected, if necessary, to a microbial elimination or sterilization treatment (for example, heating, alcohol sterilization or filtration to eliminate microbials) or a concentration treatment, and threreafter drying to produce the desired amylase inhibitor in solid form such as powders. The drying treatment may be carried out by any suitable method such as lyophilization, drying under reduced pressure, spray drying, ball drying or the like.

According to the above-mentioned process, the amylase inhibitor can be produced in high yield, which has no or very low trypsin inhibitory activity, but has a very high amylase inhibitory activity. This amylase inhibitor having a high inhibitory activity against the amylase contained in pancreatic juice, is effective for the inhibition of insulin secretion, and also is highly effective in inhibiting digestion of the cooked starch such as cooked rice or in inhibiting the hydrolysis to glucose.

The analysis of the present amylase inhibitor by a polyacrylamide electrophoresis according to the method of Davis et al. (Annals New York Academy of Sciences, vol. 121, p. 404, 1985) revealed that there was contained therein a large amount of a protein with a molecular weight of about 24000 and an electrophoretic mobility of about 0.19.

The amylase inhibitor produced by the present process can be used alone or in combination with conventional carriers or adjuvants for pharmaceutical preparation in the form of a liquid preparation or a solid preparation such as granules and tablets as an agent for inhibiting an increase in blood glucose level or an agent for controlling an insulin secretion. In addition, the amylase inhibitor may be used as food additives, particularly for carbohydrate foods rich in starch such as bread and cookie or as additives for tea, soup, seasoned fish meal and spread such as butter and jam. The amount of the amylase inhibitor administered to humans or added to foods may adequately be controlled depending upon conditions and symptoms of the subject to be administered or nature and quantity of foods to be ingested. For example, the amount of the amylase inhibitor ingested when added to foods may be in the range of about 0.1 to 20 g, preferably about 0.4 to 8 g per meal.

The invention is further illustrated by the following examples, in which the following procedure was employed for the determination of total protein content; content of a protein with an electrophoretic mobility of about 0.19 (called "0.19 AI" hereafter) when subjected to polyacrylamide electrophoresis according to the method of Davis et al. as cited above; trypsin inhibitory activity; blood glucose level and quantity of insulin.

Determination of Total Protein Content

It was determined by the Kjeldahl's method using KJELTEC AUTO 1030 analyzer manufactured by Tecator, Sweden. A nitrogen-protein conversion factor of 5.70 was adopted.

Determination of 0.19 AI Content

A test sample was dissolved in a 0.1% aqueous solution of trifluoroacetic acid, and the solution was subjected to high performance liquid chromatography under the conditions shown below, to determine the peak area for 0.19 AI in the chromatogram. On one hand, an authentic sample of 0.19 AI (purity 100%) was subjected to high performance liquid chromatography under the same condition as above to measure the peak area for 0.19 AI in the chromatogram. The 0.19 AI content in the sample was calculated according to the following equation:

0.19 AI content in the test sample (%) = (Sa/St) × 100 in which
Sa = Peak area for 0.19 AI in the test sample
St = Peak area for 0.19 AI in the authentic sample Chromatographic Conditions
Column
Packing material: CAPCELL PAK C18 SG120A (particle size 5 μm) (manufactured by Shiseido Co. Ltd.)
size: 4.6 mm φ × 250 mm
Temperature: 50° C.
Flow rate: 1 ml/min.
Detection: Absorbance at 280 nm
Mobile phase:
High pressure linear gradient elution with a time/-concentration gradient shown below, consisting of
Solution A: 0.1% aqueous solution of trifluoroacetic acid; and
Solution B: aqueous solution of 80% acetonitrile and 0.1% trifluoroacetic acid

| Time (min.) | Solution A (%) | Solution B (%) |
| --- | --- | --- |
| 0 | 65 | 35 |
| 3 | 62 | 38 |
| 15 | 62 | 38 |
| 16 | 0 | 100 |
| 20 | 0 | 100 |

Determination of trypsin inhibitory activity

It was determined in accordance with the method of Kakade [Kakade et al., Cereal Chem., vol. 51, p. 376 (1974)]. An aqueous solution of the test sample was added to an enzyme reaction system of bovine trypsin using benzoyl-DL-arginine-p-nitroanilide as substrate and a decrease in trypsin activity induced thereby was defined as a trypsin inhibitory activity expressed in terms of trypsin units inhibited (TIU). The bovine trypsin was used in an amount equivalent to 60 TU in term of the activity expression defined in the Kakade's method, and an amount of the aqueous sample solution added was adjusted so as to inhibit the enzyme reaction by 40–60%.

Determination of increase in blood glucose level

Blood glucose level was determined by the glucose oxidase method immediately after blood drawing from the forearm vein of a subject. The increase in blood level was determined by substracting the value in fasting from the value found. In the measurement according to the glucose oxidase method was used Glucose-B-test Wako (manufactured by Wako Pure Chemical Industries).

Determination of insulin level

Blood was drawn from the forearm vein of a subject and immediately centrifuged to prepare serum. Insulin level in the serum was measured by enzyme immunoassay. For the enzyme immunoassay was used Glazyme Insulin-EIA test (manufactured by Wako Pure Chemical Industries).

EXAMPLE 1

To 800 kg of wheat flour was added 110 lit. of water and the mixture was kneaded to form a dough. The dough was washed with 7600 lit. of water to recover 410 kg of gluten and 505 kg of wheat starch. At this stage, 6200 lit. of a waste liquid were produced. The pH of the waste liquid (aqueous extract) was adjusted with hydrochloric acid to 3, and after allowing to stand for 30 min., adjusted with ammonia to 6.5, by which insoluble matters were precipitated. The precipitates were removed to recover 5200 lit. of supernatant (I).

To the supernatant (I) was added 300 ppm of sodium alginate. The mixture was adjusted to pH 4.2 and stirred for 30 min, thus forming water-insoluble matters. They were recovered by means of a De Laval centrifuge. The recovered mass was dispersed in 10 times amount of water. The dispersion was mixed with 4.7 kg of calcium chloride, thoroughly stirred, adjusted with ammonia to pH 8.5 and allowed to stand for one hour. The solid matters were separated off by means of a De Laval centrifuge to recover 600 lit. of a supernatant. No lectin activity was found in the supernatant.

The supernatant recovered above was neutralized with hydrochloric acid, and the neutralized solution was heated at 80° C. for 30 min. Insoluble matters thus formed were separated by means of a De Laval centrifuge to recover a supernatant. The supernatant was concentrated by means of a ultrafiltration membrane [manufactured by Nitto Denko K.K.; NTU-3250CIR (20000 Dalton cut off)], while removing excess calcium salt to give concentration solution (II).

140 lit. of the concentration solution (II) were adjusted with ammonia to pH 7.5 and passed through a column (900 mm in length, 200 mm in inner diameter) in which 28 lit. of a cation exchange resin (Diaion HPK-55, manufactured by Mitsubishi Kasei K.K.) has been packed, at a flow rate of 1 lit./min. Fractions not adsorbed on and eluted from the cation exchange resin were collected.

The eluted fractions were filtered through a ceramic filter for elimination of microbials and then lyophilized to give 1400 g of dry powder (III).

The supernatant (I), concentrate solution (II) and dry powder (III) were determined for total protein content (%), 0.19 AI content (%) and trypsin inhibitory activity (TIU/mg). The results are shown in Table 1.

TABLE 1

| | Total protein content (%) | 0.19 AI content (%) | Trypsin inhibitory activity (TIU/mg) |
|---|---|---|---|
| Supernatant (I)* | 18 | 0.5 | 5.2 |
| Concentrate solution (II)* | 60 | 15 | 21.3 |
| Dry powder (III) | 91 | 35 | 0.8 |

*as determined in dry form

The data in Table 1 show that the amylase inhibitor produced by the process of the invention, i.e., dry powder (III), is very effective with almost no trypsin inhibitory activity associated.

EXAMPLE 2

Ten non-diabetic healthy males, after fasted for 10 hours, were each given 300 g of cooked rice and 200 ml of sugarless tea. Blood was drawn at 30 min. intervals after the meal to determine an increase in blood glucose level and an insulin level. The test was run three times in total at one week interval for each subject, by giving to the subject sugarless tea containing 0 g, 0.4 g and 2 g of dry powder (III) (amylase inhibitor) prepared in Example 1. The results are shown in Table 2.

TABLE 2

| | | Amount of dry powder (III) added (g) | | |
|---|---|---|---|---|
| | | 0 | 0.4 | 2 |
| Increase in blood glucose level (mg/dl) | | | | |
| After | 0 min. | 0 | 0 | 0 |
| | 30 min. | 74 | 63 | 20 |
| | 60 min. | 90 | 88 | 40 |
| | 90 min. | 53 | 37 | 16 |
| | 120 min. | 14 | 23 | 32 |
| Insulin level (μU/ml) | | | | |
| After | 0 min. | 7 | 8 | 7 |
| | 30 min. | 26 | 22 | 11 |
| | 60 min. | 35 | 22 | 12 |
| | 90 min. | 33 | 19 | 12 |
| | 120 min. | 26 | 18 | 11 |

The data in Table 2 show that the amylase inhibitor of the invention is effective in the inhibition of an increase in blood glucose level and an insulin secretion.

Industrial Application of the Invention

The processes of the invention can provide effective amylase inhibitors having a high amylase inhibitory activity, but substantially no trypsin inhibitory activity. Especially, the amylase inhibitors of the invention have a high inhibitory activity against the amylase contained in the pancreatic juice and thus can effectively inhibit a secretion of insulin, which are useful in the prophylaxis and treatment of diseases such as hyperglycemia, diabetes, hyperlipemia, arterioscrerosis and obesity.

Furthermore, the amylase inhibitors produced by the processes of the invention are associated with no adverse reactions such as diarrhea and nausea when ingested and are pleasant to the palate and easily ingested.

What is claimed is:

1. A process for the preparation of an amylase inhibitor which comprises the steps of:
    (a) extracting wheat, wheat flour or wheat gluten with water, a dilute acid, a dilute alkali or an aqueous alcohol to produce a solution containing the amylase inhibitor;
    (b) adding a polysaccharide to said solution to form an insoluble complex of the amylase inhibitor with the polysaccharide and separating the insoluble complex from the solution;
    (c) dissolving or dispersing said complex in a solution, the separating the polysaccharide from the solution to collect a solution containing the amylase inhibitor; and
    (d) treating the collected solution with a cation exchanger and recovering the amylase inhibitor from fractions that have not been adsorbed on the cation exchanger.

2. A process of claim 1 wherein the solution obtained in step (a) is a waste liquid or water washings discharged in the production of starch and gluten by Martin's and Batter's methods.

3. A process of claim 1 wherein the polysaccharide is selected from the group consisting of sodium alginate, carboxymethylcellulose, κ-carrageenan, ν-carrageenan, λ-carrageenan, pectin, xanthan gum and gellan gum.

4. A process of claim 1 wherein the solution containing the amylase inhibitor is subjected to a further treatment for removing contaminants therefrom prior to passing to step (b).

5. A process of claim 1 wherein the solution containing the amylase inhibitor collected in step (c) is subjected to a purification treatment prior to passing to step (d).

6. A process of claim 4 wherein the contaminants are soluble proteins.

* * * * *